United States Patent  
Kaneko et al.

(10) Patent No.: US 9,267,901 B2
(45) Date of Patent: Feb. 23, 2016

(54) METHOD FOR ESTIMATING BREAKING ENERGY AND RUBBER COMPOSITION

(71) Applicant: SUMITOMO RUBBER INDUSTRIES, LTD., Kobe-shi, Hyogo (JP)

(72) Inventors: Fusae Kaneko, Kobe (JP); Takanobu Kawamura, Kobe (JP)

(73) Assignee: SUMITOMO RUBBER INDUSTRIES, LTD., Kobe-shi (JP)

( * ) Notice: Subject to any disclaimer, the term of this patent is extended or adjusted under 35 U.S.C. 154(b) by 224 days.

(21) Appl. No.: 14/153,226

(22) Filed: Jan. 13, 2014

(65) Prior Publication Data

US 2014/0211915 A1 Jul. 31, 2014

(30) Foreign Application Priority Data

Jan. 31, 2013 (JP) ................................. 2013-017407

(51) Int. Cl.
G01N 23/06 (2006.01)
G01N 23/02 (2006.01)
G01N 23/00 (2006.01)
C08L 7/00 (2006.01)
C08L 9/00 (2006.01)

(52) U.S. Cl.
CPC . G01N 23/02 (2013.01); C08L 7/00 (2013.01); C08L 9/00 (2013.01); G01N 23/063 (2013.01); G01N 2223/623 (2013.01)

(58) Field of Classification Search
USPC .......... 378/51, 53, 61, 64, 83, 98.6, 98.9, 210
See application file for complete search history.

(56) References Cited

U.S. PATENT DOCUMENTS

| 8,754,159 | B2* | 6/2014 | Miyazaki | B60C 1/0016 524/492 |
| 2010/0218864 | A1* | 9/2010 | Takaku | C08J 3/215 152/157 |
| 2012/0172491 | A1* | 7/2012 | Miyazaki | B60C 1/0016 523/157 |
| 2013/0226470 | A1* | 8/2013 | Kaneko | G01N 23/00 702/34 |
| 2013/0296493 | A1* | 11/2013 | Yamamoto | C08C 19/20 525/102 |
| 2014/0099723 | A1* | 4/2014 | Kaneko | G01N 23/2273 436/85 |
| 2014/0349407 | A1* | 11/2014 | Kaneko | G01N 23/063 436/85 |

FOREIGN PATENT DOCUMENTS

| JP | 8-61434 | A | 3/1996 |
| JP | 8-187216 | A | 7/1996 |
| JP | 2000-26156 | A | 1/2000 |
| JP | 2009-511532 | A | 3/2009 |
| JP | 2012-140507 | A | 7/2012 |
| JP | 2012-141278 | A | 7/2012 |

OTHER PUBLICATIONS

Kaneko et al., "Preprints of the Joint Symposium on the annual meeting of Japan Synchrotron Radiation Science", 2011, pp. 119.

* cited by examiner

*Primary Examiner* — Bernard E Souw
(74) *Attorney, Agent, or Firm* — Birch Stewart Kolasch & Birch, LLP

(57) ABSTRACT

The present invention provides a method for estimating breaking energy of a rubber material, in particular breaking energy of a surface of a rubber material. The present invention also provides to a rubber composition excellent in crack resistance. The present invention relates to a method for estimating breaking energy of a rubber material, including determining a carbon-carbon double bond content in the rubber material.

5 Claims, 1 Drawing Sheet

METHOD FOR ESTIMATING BREAKING ENERGY AND RUBBER COMPOSITION

TECHNICAL FIELD

The present invention relates to a method for estimating breaking energy of a rubber material. The present invention also relates to a rubber composition excellent in crack resistance.

BACKGROUND ART

To analyze the initial performance of rubber products or the performance of aged rubber products, the following method is widely used: dumbbell specimens cut out of the products are broken to measure the elongation at break (%) and tensile strength (MPa) using a tensile tester according to JIS-K 6251 "Rubber, vulcanized or thermoplastic-Determination of tensile stress-strain properties", and the breaking energy (the area below a stress-elongation curve) is then calculated from the resultant values.

A typical tensile test requires the preparation of a specimen of 35 to 120 mm in width, 6 to 25 mm in length, and 2 mm in thickness without any cracks and the like to provide accurate test results. This requires cutting a sheet-shaped specimen out of a product and then cutting the specimen into a dumbbell shape, which is greatly time-consuming. Moreover, though the initial performance can be analyzed according to this method, it is impossible in practice to perform the tensile test on deteriorated samples because many of such deteriorated samples have cracks and thus are difficult to prepare to obtain evaluable specimens. Thus, determination of the breaking energy in accordance with JIS-K 6251 has various disadvantages.

Meanwhile, since high breaking energy is generally considered to be important for the securement of good deterioration resistance, in particular crack resistance, rubber compositions excellent in crack resistance have been developed on the basis of their breaking energy values. However, the breaking energy varies depending on the formulation or vulcanizing conditions though it is an important parameter. Therefore, it is considered to be further important to determine the breaking energy of aged rubber materials in accordance with JIS-K 6257 "Rubber, vulcanized or thermoplastic—Determination of heat ageing properties" for evaluation of crack resistance.

However, the tensile test cannot be performed on deteriorated samples due to the difficulty in preparing evaluable specimens therefrom as described above. Therefore, it is also difficult to develop a rubber composition excellent in crack resistance referring to the breaking energy as an indicator.

SUMMARY OF INVENTION

Technical Problem

The present invention aims to solve the above problems and to provide a method for estimating breaking energy of a rubber material, in particular breaking energy of a surface of a rubber material. The present invention also aims to provide a rubber composition excellent in crack resistance.

Solution to Problem

The present invention relates to a method for estimating breaking energy of a rubber material, including determining a carbon-carbon double bond content in the rubber material.

In the method for estimating breaking energy, the carbon-carbon double bond content is preferably determined by irradiating the rubber material with high intensity X-rays and measuring X-ray absorption while varying the energy of the X-rays.

In the method for estimating breaking energy, the rubber material is preferably comprised of a rubber composition for tires.

The present invention also relates to a rubber composition, comprising a rubber material having a carbon-carbon double bond content of 40% or more. The rubber material preferably has a breaking energy of 3,000 MJ/m$^3$ or higher.

Advantageous Effects of Invention

Since the method for estimating breaking energy of a rubber material of the present invention includes determining a carbon-carbon double bond content in the rubber material, the breaking energy of a rubber material, in particular of a surface of a rubber material can be estimated in detail. Thus, the breaking energy can be estimated regardless of whether the rubber material is fresh or deteriorated. Also, a rubber composition forming a rubber material that has at least predetermined carbon-carbon double bond content can secure excellent crack resistance.

DESCRIPTION OF EMBODIMENTS

The method for estimating breaking energy of the present invention includes determining a carbon-carbon double bond content in a rubber material.

Figure 1:
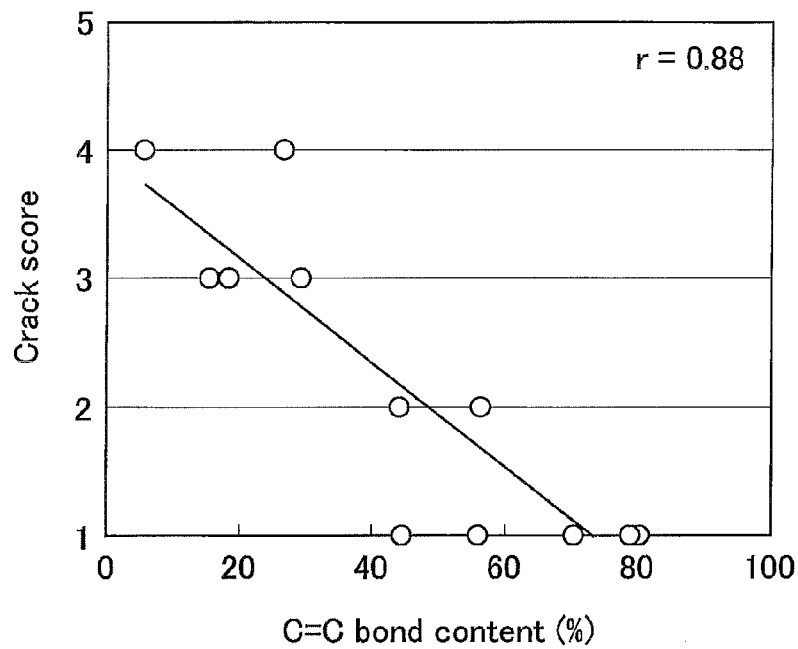
FIG. 1 shows an exemplary correlation diagram between carbon-carbon double bond content and crack score.

FIG. 1 shows a correlation between the carbon-carbon double bond content (C═C bond content) on the surface of a tire and the crack score of a sidewall of the tire, where the C═C bond content is determined by Near Edge X-ray Absorption Fine Structure (NEXAFS) method in which an X-ray absorption spectrum near the absorption edge of a specific target element is measured using high intensity X-rays. FIG. 1 demonstrates that crack scores correlate with C═C bond contents with a correlation coefficient r of 0.88. From this point, breakage of C═C bonds in a polymer is considered to lead to the occurrence of cracks, which is in turn expected to cause reduction in breaking energy. This finding leads to the hypothesis that the C═C bond content in a polymer may correlate with the breaking energy.

Figure 2:
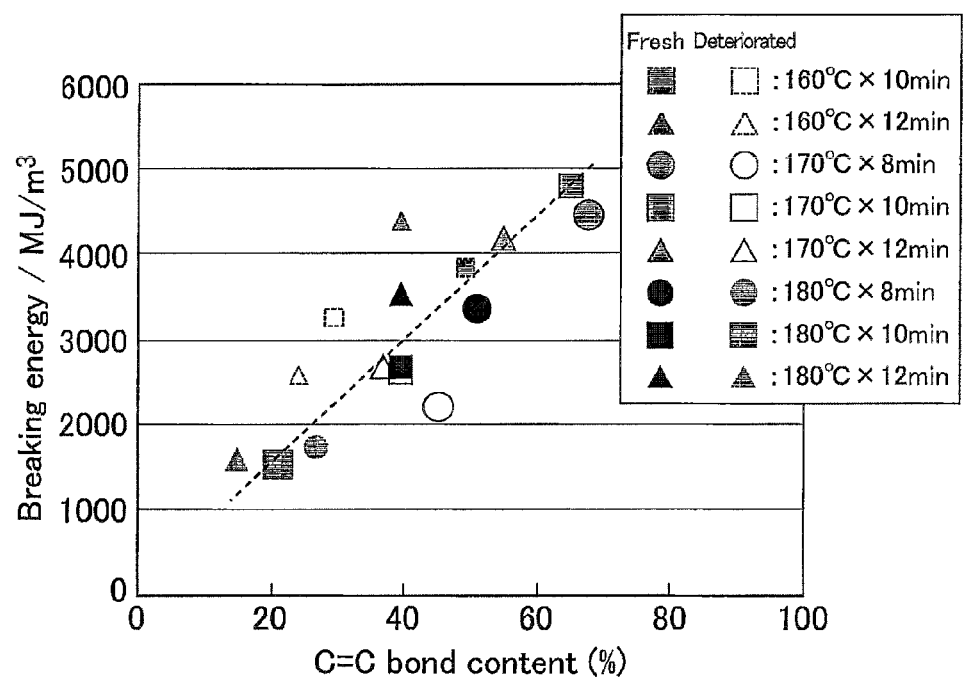
FIG. 2 shows exemplary relations between carbon-carbon double bond content and breaking energy in (fresh and deteriorated) rubber materials.

Then, the relation between the C═C bond content in a polymer measured by NEXAFS method and the breaking energy was determined. FIG. 2 shows relations between the breaking energy and the C═C bond content in (fresh) rubber materials vulcanized under different conditions and (deteriorated) rubber materials obtained by aging the rubber materials in an accelerated aging test described in JTS-K 6257. This FIG. 2 shows relations between the breaking energy and the retention ratio (%) of the C═C bond content in a particular rubber material to the C═C bond content in the corresponding raw material polymer (standard: 100%), where the raw material polymer refers to a polymer (e.g. natural rubber, butadiene rubber) that is a raw material of the rubber material under test; and the C═C bond content in the raw material polymer is determined by performing the NEXAFS measurement only on the raw material polymer. FIG. 2 reveals that the C=C bond content (the retention ratio of the C=C bond content) correlates with the breaking energy with a correlation coefficient r of 0.79, regardless of the difference in the vulcanizing conditions or whether the rubber material is fresh or deteriorated. Therefore, the breaking energy of rubber materials having the same formulation can be estimated regardless of the vulcanizing conditions and the degree of deterioration.

As described, according to the present invention, the use of the correlation line between the breaking energy and the C=C bond content (the retention ratio (%) of the C=C bond content in a rubber material to the C=C bond content in a raw material polymer of the rubber material) enables to estimate breaking energy through a simple method which includes determining the C=C bond content in a rubber material by NEXAFS method or the like, without performing a tensile test.

The rubber material usable in the method of the present invention is not particularly limited, and any conventionally known rubber compositions, such as rubber compositions containing a rubber component and other components, can be used.

Examples of the rubber component include diene rubbers such as natural rubber (NR), isoprene rubber (IR), butadiene rubber (BR), styrene-butadiene rubber (SBR), acrylonitrile butadiene rubber (NBR), chloroprene rubber (CR), butyl rubber (IIR), halogenated butyl rubber (X-IIR), and styrene-isoprene-butadiene rubber (SIBR). The rubber component may contain at least one modifying group such as a hydroxyl group and an amino group.

The rubber component may be a composite material of the rubber component with one or more resins. The resin is not particularly limited and examples thereof include those generally used in the rubber industry, such as petroleum resins such as C5 aliphatic petroleum resins and cyclopentadiene petroleum resins.

The rubber material may appropriately contain compounding agents conventionally known in the rubber industry, including fillers such as carbon black and silica, silane coupling agents, zinc oxide, stearic acid, oils, waxes, antioxidants, vulcanizing agents, vulcanization accelerators, and cross-linking agents. Such a rubber material (or rubber composition) may be prepared by any conventional kneading method and the like. Examples of such a rubber material include rubber materials for tires (rubber compositions for tires).

In the present invention, the carbon-carbon double bond content (C=C bond content) in a rubber material is determined. Here, the C=C bond content may be determined by, for example, Near Edge X-ray Absorption Fine Structure (NEXAFS) method, infrared spectroscopy (FT-IR), magnetic resonance (NMR) method, or X-ray photoelectron spectroscopy (XPS). Among them, NEXAFS method is suitable because the method enables measurement of the amount of broken C=C bonds resulting from surface deterioration; it can measure even very small samples as high intensity X-rays having a very small spot size are used in the measurement; and samples can be prepared with less effort, which saves much manpower.

The NEXAFS method, which includes scanning the X-ray energy, requires a continuous X-ray generator as a light source. In addition, an X-ray absorption spectrum with a high S/N ratio and a high S/B ratio is then required for a detailed analysis of the chemical state. Hence, most suitable for the NEXAFS measurement is a synchrotron which is a continuous X-ray source and emits X-rays having a brilliance of at least $10^{10}$ (photons/s/mrad$^2$/mm$^2$/0.1% bw), where the "bw" refers to a band width of X-rays emitted from a synchrotron.

The brilliance (photons/s/mrad$^2$/mm$^2$/0.1% bw) of the high intensity X-rays is preferably $10^{10}$ or higher, and more preferably $10^{12}$ or higher. The upper limit of the brilliance is not particularly limited. The number of photons (photons/s) of the high intensity X-rays is preferably $10^7$ or greater, and more preferably $10^9$ or greater. The upper limit of the number of photons is not particularly limited. The energy range to be scanned with the high intensity X-rays is preferably 4,000 eV or lower, more preferably 1,500 eV or lower, and further preferably 1,000 eV or lower. The lower limit thereof is not particularly limited.

Three typical methods for NEXAFS measurement are transmission method, fluorescence method, and electron yield method. For example, the method described in JP 2012-141278 A (which is incorporated by reference in the entirety) may be used. Though electron yield method is used in the examples of the present invention, the present invention is not limited to this method and various detection methods may be used. Any of these methods may be combined and simultaneously performed in the measurement.

Measuring an X-ray absorption spectrum of a rubber material by the electron yield method and analyzing the spectrum determines the C=C bond content in the rubber material (the retention ratio (%) of the C=C bond content in the rubber material to the C=C bond content in a raw material polymer contained in the rubber material (standard: 100%)). Specifically, measurement of a spectrum near the carbon K-shell absorption edge, for example, may be performed to determine the C=C bond content.

The following will specifically describe an analyzing method using spectra near the carbon K-shell absorption edge.

The C=C bond content in a rubber material (a sample) may be determined by, for example, a method including: calculating normalization constants $\alpha$ and $\beta$ using the following Formula 1 on the basis of X-ray absorption spectra obtained by scanning over a required range of high intensity X-ray energies at the carbon K-shell absorption edge within the range of 260 eV to 400 eV; performing waveform separation of the X-ray absorption spectra at the carbon K-shell absorption edge corrected with the normalization constants $\alpha$ and $\beta$ to obtain peak areas derived from $\pi^*$ transition at around 285 eV; and determining the C=C bond content in the rubber material using the following Formula 2 with the obtained peak areas:

[total area of X-ray absorption spectrum over measurement range of unvulcanized polymer]×α=1,
and

[total area of X-ray absorption spectrum over measurement range of rubber material]]×β=1; and    (Formula 1)

[(peak area of π* of rubber material)×β]/[(peak area of π* of unvulcanized polymer)×α]×100=[C=C bond content (%) of rubber material].    (Formula 2)

Since the peak assigned to $\pi^*$ transition at around 285 eV corresponds to C=C bond, the C=C bond content (%) of rubber materials can be determined by the above method.

In the method for determining the C=C bond content, the range of high intensity X-ray energies is preferably set to 260 to 350 eV. In the method for determining the C=C bond content, the background is assessed based on a slope before the absorption edge and subtracted prior to the operation of the foregoing Formula 1.

In the method for determining the C=C bond content, the total area of the X-ray absorption spectrum in Formula 1 is the integral of the spectrum over the measurement range. The energy range can be changed according to the measurement conditions, etc.

In the method for determining the C=C bond content, it is difficult for NEXAFS method to perform an absolute measurement because subtle changes in the distance from the light source to the sample or other parameters affect the magnitude of the X-ray absorption spectrum. For this reason, the results of NEXAFS measurement of the carbon K-shell absorption edge cannot be simply compared between samples. Hence, normalization is first carried out using Formula 1 to directly compare the π* peaks of the samples. Next, the C=C bond content is determined according to Formula 2 based on the normalized spectra. The analysis may be specifically performed by the method described in JP 2012-141278 A (which is incorporated by reference in the entirety).

In the method for determining the C=C bond content in a rubber material, peak intensities may also be used instead of the peak areas in Formula 2 to similarly determine the C=C bond content.

Then, a correlation diagram as shown in FIG. 2 can be prepared from the thus obtained C=C bond contents (%) of rubber materials and the measured values of breaking energy determined by performing a tensile test on the rubber materials from which predetermined specimens can be prepared. Thus, such a correlation diagram enables estimation of the breaking energy of a rubber material even when a tensile test cannot be performed on the rubber material.

The rubber composition of the present invention forms a rubber material having a carbon-carbon double bond content of 40% or more. That is, in the rubber composition, the retention ratio (%) of the C=C bond content in the rubber material to the C=C bond content in a raw material polymer contained in the rubber material (standard: 100%) is 40% or more.

Since the estimation method enables estimation of the breaking energy of samples with cracks or the like, the method provides an indicator for preparation of a rubber composition excellent in crack resistance. Accordingly, when the estimation method is used to estimate breaking energy and then the rubber material is found to have at least predetermined carbon-carbon double bond content, a rubber composition forming the rubber material has excellent crack resistance due to high C=C bond content.

Specifically, in FIG. 1, which shows a correlation diagram between the crack score and the C=C bond content, products having a crack score of 1 to 2 are less likely to lead to complaints from users, whereas products having a crack score of 3 often lead to complaints from users. Thus, fresh rubber materials are considered to require a C=C bond content of at least 40%, which is calculated by subtracting 30% corresponding to a crack score of around 2.5, which is considered to nearly lead to complaints from users, from 70%, which is the average C=C bond content of fresh rubber materials. Therefore, a rubber composition having a C=C bond content ratio based on the C=C bond content in a raw material of 40% or more can be a rubber composition having favorable crack resistance.

The rubber material preferably has a breaking energy of 3,000 MJ/m$^3$ or higher. The breaking energy can be determined by, for example, applying the value of C=C bond content of the rubber material to the correlation line.

Specifically, in the correlation line between breaking energy and C=C bond content in (fresh and deteriorated) rubber materials in FIG. 2, since a fresh rubber material having a C=C bond content of 40% or more corresponds to a rubber composition excellent in crack resistance, the correlation line indicates that a breaking energy of 3,000 MJ/m$^3$ or higher can result in favorable crack resistance.

In this manner, the measurement of the breaking energy of a fresh rubber material enables the preparation of a rubber composition excellent in crack resistance without determining the breaking energy of the aged rubber material in accordance with JIS-K 6257 "Rubber, vulcanized or thermoplastic—Determination of heat ageing properties". In addition, the measurement of the C=C bond content also enables the preparation of a rubber composition excellent in crack resistance.

The rubber composition of the present invention may be prepared by any ordinary method. Specifically, for example, the rubber composition may be prepared by a method including kneading the above-described components with a Banbury mixer, kneader, open roll mill, or the like and then vulcanizing the kneaded mixture. The rubber composition can be used for tire components, especially suitably for treads and sidewalls, for example.

The present invention can also provide a pneumatic tire produced from the rubber composition by a conventional method. The pneumatic tire may be produced by a method including: extruding an unvulcanized rubber composition containing the above components into the shape of a tire component such as a sidewall or a tread; molding the tire component along with other tire components in a tire building machine in a conventional manner to prepare an unvulcanized tire; and heating and pressurizing the unvulcanized tire in a vulcanizer.

EXAMPLES

The present invention is described in greater detail with reference to, but not limited to, the following examples.

<Preparation of Crosslinked Rubber Compositions 1 and 2>

The materials other than the sulfur and vulcanization accelerator in amounts shown in the formulation below were charged into a 1.7-L Banbury mixer (product of Kobe Steel, Ltd.) to give a fill factor of 58%. The materials were then kneaded at 80 rpm until the temperature reached 140° C. (Step 1). The sulfur and vulcanization accelerator in amounts shown in the formulation below were added to a kneaded mixture prepared in Step 1, and the resultant mixture was kneaded and vulcanized in the conditions below, thereby providing a crosslinked rubber composition 1 or 2 (Step 2).

(Formulation)

Natural rubber (50 parts by mass), butadiene rubber (50 parts by mass), carbon black (60 parts by mass), oil (5 parts by mass), an antioxidant (4 parts by mass), wax (2.5 parts by mass), zinc oxide (3 parts by mass), stearic acid (2 parts by mass), sulfur powder (1.2 parts by mass), and a vulcanization accelerator (1 part by mass).

The materials used are listed below.

Natural rubber: TSR 20
Butadiene rubber: BR 150B (Ube industries, Ltd.)
Carbon black: SHOBLACK N351 (Cabot Japan K. K.)
Oil: Process X-140 (Japan Energy Corporation)
Antioxidant: NOCRAC 6C
(N-1,3-dimethylbutyl-N'-phenyl-p-phenylenediamine) (Ouchi Shinko Chemical Industrial Co., Ltd.)
Wax: OZOACE 0355 (Nippon Seiro Co., Ltd.)
Zinc oxide: Ginrei R (Toho Zinc Co., Ltd.)
Stearic acid: TSUBAKI (NOF Corporation)

Sulfur powder (containing 5% of oil): 5% oil-treated sulfur powder (soluble sulfur containing 5% by mass of oil) (Tsurumi Chemical Industry Co., Ltd.)
Vulcanization accelerator: NOCCELER CZ (N-cyclohexyl-2-benzothiazylsulfenamide) (Ouchi Shinko Chemical Industrial Co., Ltd.)
(Vulcanizing Conditions)
Crosslinked rubber composition 1: 170° C., 10 minutes
Crosslinked rubber composition 2: 180° C., 8 minutes
<Preparation of Deteriorated Crosslinked Rubber Compositions 3 and 4>

The prepared crosslinked rubber compositions 1 and 2 were aged according to an accelerated aging test described in JIS-K 6257 to prepare deteriorated crosslinked rubber compositions 3 and 4, respectively.
<New Tire and Old Tires 1 and 2>

Tires having the same formulation as the crosslinked rubber composition 1 were used. The lapse of time from the manufacture of each tire was as follows.
New tire: fresh
Old tire 1: 3.5 years after manufacture
Old tire 2: 5.0 years after manufacture
(Preparation of Specimens)

The prepared crosslinked rubber compositions 1 and 2, deteriorated crosslinked rubber compositions 3 and 4, new tire, and old tires 1 and 2 were punched into #3 dumbbell specimens. Each of the prepared specimens was evaluated as described below. Table 1 shows the results. Here, the estimated values of breaking energy were obtained based on a correlation line determined from the C=C bond contents (%) and the calculated values (measured values) of breaking energy of the crosslinked rubber compositions 1 and 2 and deteriorated crosslinked rubber compositions 3 and 4.

1. Measurement of Breaking Energy

The tensile strength and the elongation at break of each of the specimens were measured in accordance with JIS-K 6251 "Rubber, vulcanized or thermoplastic—Determination of tensile stress-strain properties". Thereafter, the breaking energy was calculated according to the formula: (tensile strength)×(elongation at break)/2.

2. Measurement of C=C Bond Content

Using NEXAFS, each of the specimens was analyzed for C=C bond content (%) as follows. The device used and measurement conditions in the NEXAFS measurement were as described below. The specimens to be measured were processed with a microtome such that the thickness of each specimen was 100 μm or thinner, and thereafter stored in a vacuum desiccator.
(Device Used, Measurement Conditions)
NEXAFS: NEXAFS measurement device provided with the beamline BL12 at Kyushu Synchrotron Light Research Center (SAGA-LS)
Brilliance: $5\times10^{12}$ photons/s/mrad$^2$/mm$^2$/0.1% bw
Number of photons: $2\times10^9$ photons/s
Photon energy range measured: 275 eV to 320 eV
(C=C Bond Content Analysis)

By scanning a sample over a range of high intensity X-ray energies of 260 to 400 eV, X-ray absorption spectra at the carbon K-shell absorption edge was obtained. Subsequently, normalization constants α and β were calculated according to Formula 1 based on the spectra over the required range of 260 to 350 eV. The spectra were then normalized (corrected) with the constants. The normalized spectra were subjected to waveform separation and the C=C bond content (%) was then determined according to Formula 2 based on the resulting peak areas derived from π* transition at around 285 eV.

In the C=C bond content analysis, the unvulcanized polymer sample was prepared as follows.

Natural rubber (0.5 g) and butadiene rubber (0.5 g) were dissolved in toluene (30 ml), and then reprecipitated in methanol (300 ml) to remove unwanted chemicals and the like in the polymers. Thereafter, the resultant precipitate was redissolved in toluene (30 ml) and spin-coated on a silicon wafer to provide a thin film.

TABLE 1

|  | Crosslinked rubber composition 1 | Crosslinked rubber composition 2 | Deteriorated crosslinked rubber composition 3 | Deteriorated crosslinked rubber composition 4 | New tire | Old tire 1 | Old tire 2 |
|---|---|---|---|---|---|---|---|
| C=C bond content (%) | 64.8 | 39.4 | 39.4 | 21.1 | 60.7 | 31.6 | 7.6 |
| Calculated breaking energy (MJ/m$^3$) | 4780 | 2640 | 2624 | 1494 | 4420 | Unmeasurable | Unmeasurable |
| Estimated value of breaking energy (MJ/m$^3$) | 4787 | 2690 | 2690 | 1500 | 4550 | 2190 | 427 |
| Complaint score | 1 | 1 | 2 | 4 | 1 | 3 | 5 |

The old tires 1 and 2 had too many cracks to carry out the tensile test and it was therefore impossible to calculate the breaking energy from measured values. However, values of breaking energy were estimated and calculated like other specimens, based on a correlation line determined from the data of crosslinked rubber compositions 1 and 2 and deteriorated crosslinked rubber compositions 3 and 4.

The (fresh) crosslinked rubber composition 2 had a C=C bond content below 40%, whereas the deteriorated crosslinked rubber composition 4, which was prepared by deteriorating the crosslinked rubber composition 2, had a lower C=C bond content of 21.1%, and the complaint score also deteriorated from 1 to 4. The results revealed that the crosslinked rubber composition 2 was a rubber material of a grade that would lead to complaints from users.

The invention claimed is:

1. A method for estimating breaking energy of a rubber material, comprising determining a carbon-carbon double bond content in the rubber material.

2. The method for estimating breaking energy according to claim 1,
wherein the carbon-carbon double bond content is determined by irradiating the rubber material with high intensity X-rays and measuring X-ray absorption while varying the energy of the X-rays.

3. The method for estimating breaking energy according to claim 1,
   wherein the rubber material is comprised of a rubber composition for tires.

4. A rubber composition, comprising a rubber material having a carbon-carbon double bond content of 40% or more.

5. The rubber composition according to claim 4,
   wherein the rubber material has a breaking energy of 3000 MJ/m$^3$ or higher.

* * * * *